United States Patent [19]

Parry

[11] Patent Number: 5,104,384
[45] Date of Patent: Apr. 14, 1992

[54] INJECTION DEVICES

[75] Inventor: John S. Parry, Stroud, England

[73] Assignee: Sterimatic Holdings Limited, Stroud, England

[21] Appl. No.: 640,310

[22] PCT Filed: Sep. 21, 1989

[86] PCT No.: PCT/GB89/01112

§ 371 Date: Jan. 25, 1991

§ 102(e) Date: Jan. 25, 1991

[87] PCT Pub. No.: WO90/03815

PCT Pub. Date: Apr. 19, 1990

[30] Foreign Application Priority Data

Oct. 5, 1988 [GB] United Kingdom ............... 8823349
May 4, 1989 [GB] United Kingdom ............... 8910251

[51] Int. Cl.⁵ .................................... A61M 5/32
[52] U.S. Cl. ......................... 604/192; 604/198; 604/263
[58] Field of Search ............ 604/198, 192, 187, 263, 604/110

[56] References Cited

U.S. PATENT DOCUMENTS

| | | |
|---|---|---|
| 2,693,186 | 11/1954 | Riker et al. |
| 2,876,770 | 3/1959 | White |
| 2,888,924 | 6/1959 | Dunmire |
| 3,134,380 | 5/1964 | Armao |
| 3,534,735 | 10/1970 | Sly |
| 3,580,255 | 5/1971 | Cimber |
| 4,139,009 | 2/1979 | Alvarez |
| 4,425,120 | 1/1984 | Sampson et al. |
| 4,573,976 | 3/1986 | Sampson et al. |
| 4,664,654 | 5/1987 | Strauss |
| 4,666,435 | 5/1987 | Braginetz |
| 4,681,567 | 7/1987 | Masters et al. |
| 4,695,274 | 9/1987 | Fox |
| 4,702,738 | 10/1987 | Spencer |
| 4,775,369 | 10/1988 | Schwartz |
| 4,778,453 | 10/1988 | Lopez |
| 4,795,432 | 1/1989 | Karczmer |

FOREIGN PATENT DOCUMENTS

| | | |
|---|---|---|
| 0268445 | 5/1988 | European Pat. Off. |
| 858913 | 1/1961 | United Kingdom |
| 2178322 | 2/1987 | United Kingdom |

Primary Examiner—John D. Yasko
Attorney, Agent, or Firm—Young & Thompson

[57] ABSTRACT

An accessory for an injection device comprises a protective sleeve 1 for surrounding the needle 2 and has inner and outer sleeve parts 3, 5 which are movable relative to one another from a contracted position, in which the point of the needle projects from the sleeve to enable an injection to be effected, to an extended position, in which the point of the needle is shielded by the sleeve. The sleeve parts 3, 5 are guided relative to one another by a projection on the inner sleeve part 3 engaging within a track 14A in the outer sleeve part 5. At least a portion of the track 14A is formed by a slot 15 extending through the wall of a collar 6 which is separately formed from the remainder of the outer sleeve part 5 and which is fitted within an end portion of the remainder of the outer sleeve part 5 when the accessory is assembled. Such an arrangement provides for ease of fabrication and assembly.

10 Claims, 3 Drawing Sheets

INJECTION DEVICES

FIELD OF THE INVENTION

This invention relates to injection devices, such as syringes, and accessories therefor.

BACKGROUND OF THE INVENTION

After use of a syringe to perform an injection or take up a sample of blood from a patient, there is a risk that doctors or nurses will accidentally prick themselves with the needle of the syringe. This phenomenon is known as "needle stick" and can be highly dangerous due to the risk of transfer of blood-related diseases.

DESCRIPTION OF THE RELATED ART

European Patent Specification No. 0268445A discloses an accessory for an injection device of the kind in which liquid is drawn or expelled along a hollow needle, the accessory comprising a protective sleeve for surrounding the needle and having two sleeve parts which are movable relative to one another in the direction of the length of the needle from a contracted position, in which the point of the needle projects from the sleeve to an extent to enable an injection to be effected, to an extended position, in which the point of the needle is located within the sleeve to shield the point of the needle. Such an accessory will be referred to hereinafter as "an accessory of the type referred to".

In order to substantially eliminate the danger of needle stick after the injection has been performed, the disclosed accessory includes retaining means for retaining the sleeve in the extended position after the injection has been effected and for preventing the point of the needle from being exposed solely by application of pressure to the end of the sleeve in the direction of contracting movement and biasing means for resiliently biasing the sleeve towards its extended position.

It is to be understood that the term "injection device" is used in this context to cover both a device, such as a syringe or a drip feed, for introducing a substance into a site penetrated by a needle, and a device, such as a blood collection needle, for taking up a substance from a site penetrated by a needle.

OBJECTION OF THE INVENTION

It is an object of the present invention to provide an improvement of the accessory of the type referred to.

SUMMARY OF THE INVENTION

According to the present invention there is provided an accessory of the type referred to, in which the sleeve parts comprise an inner sleeve part and an outer sleeve part, and in which the two sleeve parts are guided relative to one another by a projection on one sleeve part engaging within a track in the other sleeve part, wherein at least a portion of the track is formed by a slot extending through the wall of a collar forming a portion of said other sleeve part which is separately formed from the remainder of said other sleeve part and which is fitted to an end portion of the remainder of said other sleeve part when the accessory is assembled.

Preferably the projection is provided on an outer surface of the inner sleeve part and the track is provided in an inner surface of the outer sleeve part, and the collar forms a portion of the outer sleeve part and is fitted within an end portion of the remainder of the outer sleeve part.

Such an arrangement is advantageous as it enables the projection on the inner sleeve part to be engaged within the slot in the collar prior to assembly of the collar within the end portion. Also it provides for ease of forming of the track during manufacture since a through-slot having a complex shape can easily be formed in the wall of the collar prior to insertion of the collar such that the end portion surrounds the portion of the collar in which the slot is formed. This avoids the need to form a track of complex shape in the inner wall of the outer sleeve part by means of an inner mandrel from which the outer sleeve part must be subsequently removed and avoids distortion of the shape of the track caused by deformation of the outer sleeve part on removal from the inner mandrel.

The invention also provides an accessory of the type referred to in which retaining means are provided for retaining the sleeve in a partially contracted position in which the point of the needle projects from the sleeve only to an extent necessary to enable the point of the needle to be located at the intended site of injection, and in which the two sleeve parts are guided relative to one another by a projection on one part engaging within a track in the other part, said track including a substantially straight portion along which the projection travels when the sleeve moves from its partially contracted position to its contracted position in which the point of the needle projects from the sleeve to an extent to enable an injection to be effected, wherein said track portion is enclosed by the sleeve so that the projection is not accessible from outside the sleeve, and said track portion extends in the direction of the length of the needle so that there is no relative twisting between the two sleeve parts as the sleeve moves from its partially contracted position to its contracted position.

It is a particular advantage of such an accessory that the sleeve can be held in a partially retracted position so as to enable the point of the needle to be accurately located at the intended site of injection, and that subsequent movement of the sleeve to the fully contracted position during performance of an injection is achieved with the projection travelling along the straight portion of the track so that there is no relative twisting between the two parts of the sleeve during such movement. It has been shown during field trials that, when such twisting occurs, this is resisted by frictional engagement of the end of the sleeve with the skin of the patient so that the two parts of the sleeve tend to lock together so that they cannot slide freely to enable the injection to be properly effected.

The invention also provides an accessory of the type referred to, in which retaining means are provided for retaining the sleeve in the extended position after the injection has been effected and for preventing the point of the needle from being exposed solely by application of pressure to the end of the sleeve in the direction of contracting movement, wherein the retaining means comprises, on one of the sleeve parts, a locking tongue within a cutout in the wall of the sleeve part, the locking tongue being pivotable within the cutout between a locking position and a disengaged position and being resiliently biased towards its locking position, and, on the other sleeve part, a shoulder which is positioned such that, during movement of the sleeve from its contracted position to its extended position, the locking tongue overrides the shoulder and, in so doing, is pivoted from it disengaged position into its locking position by resilient action so that it engages behind the shoulder to retain the sleeve in its extended position.

BRIEF DESCRIPTION OF THE DRAWINGS

In order that the invention may be more fully understood, a preferred embodiment of the invention will now be described, by way of example, with reference to the accompanying drawings, in which.

DETAILED DESCRIPTION OF THE INVENTION

Figure 1:
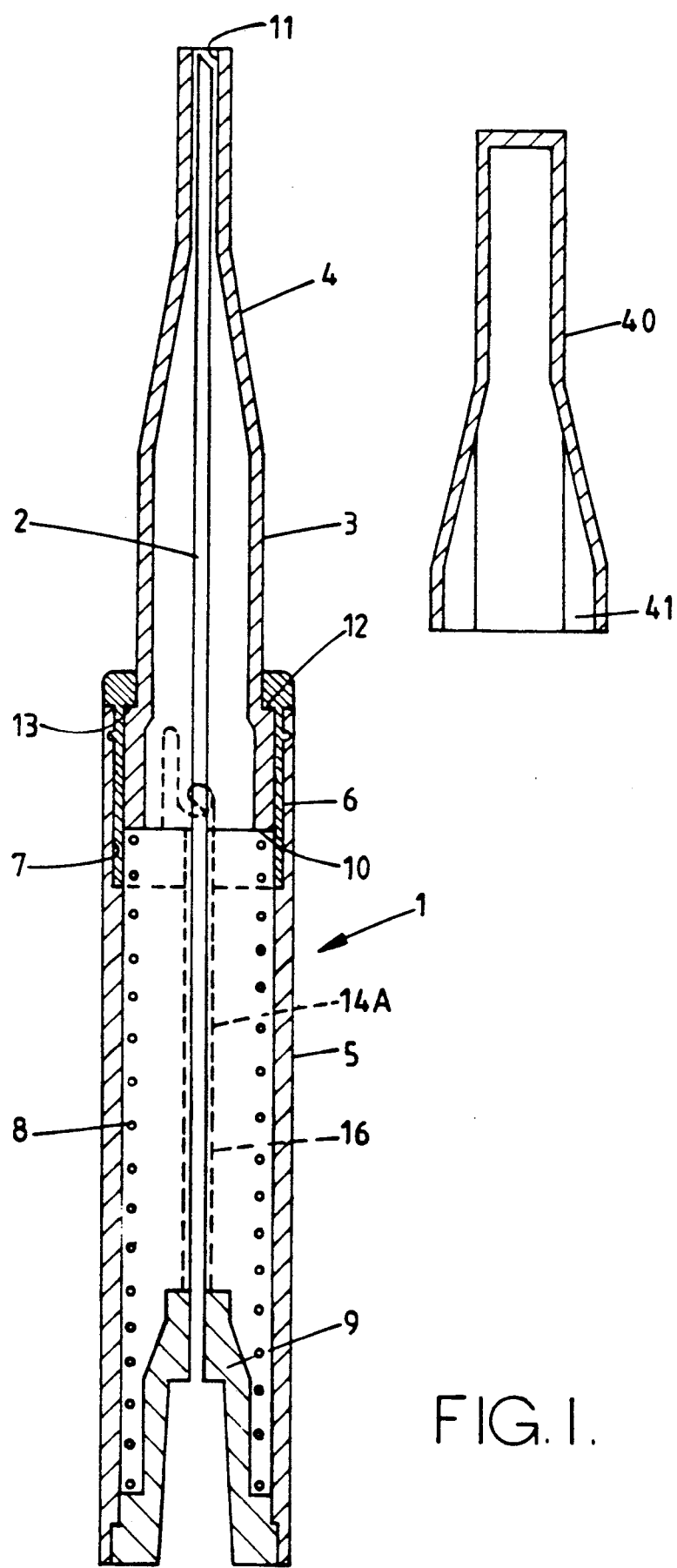
FIG. 1 is a longitudinal section through the accessory in a final locked position.

Referring to FIG. 1, the accessory shown therein comprises a protective sleeve 1 integrally formed with a hollow needle 2. The sleeve 1 consists of an inner sleeve part 3 having a tapered end portion 4 and an outer sleeve part 5. The outer sleeve part 5 has a collar 6 which is a snap fit within an annular recess 7 in the inside surface of an end portion of the outer sleeve part 5. Furthermore the outer sleeve part 5 is provided with a connector 9 through which the needle 2 extends and by means of which the sleeve 1 is attached to the outlet of a syringe.

A compression spring 8 is accommodated within the outer sleeve part 5 and acts between the connector 9, which is fixed in position as by sonic welding, and a shoulder 10 on the inside surface of the inner sleeve part 3. The inner and outer sleeve parts 3 and 5 are fitted together so that the inner sleeve part 3 is capable of being telescoped within the outer sleeve part 5 against the action of the spring 8 in order to enable the point of the needle 2 to project through an aperture 11 at the end of the inner sleeve part 3 to an extent to permit an injection to be effected, but so that the inner sleeve part 3 is automatically moved into an extended position, as shown in FIG. 1, to shield the point of the needle when the injection has been carried out, as will be described more fully below.

Figure 4:
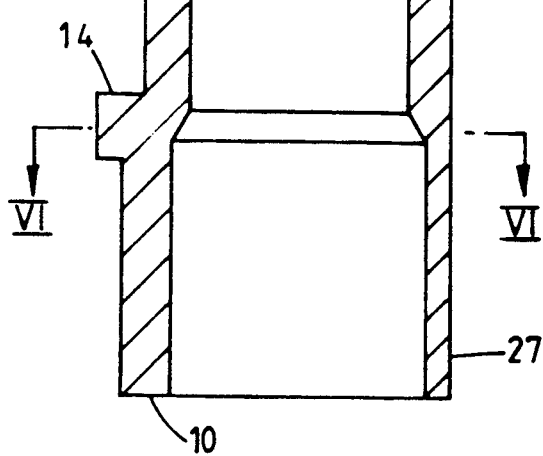
FIG. 4 is a longitudinal section through the inner sleeve part taken along the line IV—IV in FIG. 6.

The inner sleeve part 3 is retained in engagement with the outer sleeve part 5 when in its extended position by engagement of an annular shoulder 12 on the outside of the inner sleeve part 3 with an annular shoulder 13 on the inside of the collar 6. Furthermore the outside surface of the inner sleeve part 3 has an outwardly extending projection 14 (see FIG. 4 which shows the part 3 in longitudinal section transverse to the longitudinal section of FIG. 1) which engages within a track 14A (shown in broken lines) on the inside surface of the outer sleeve part 5 including the collar 6.

Figure 2:
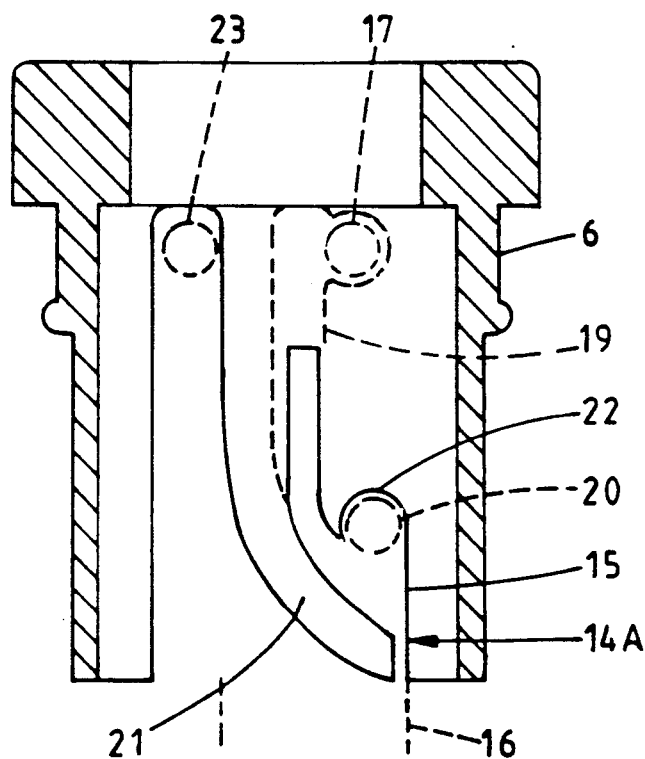
FIG. 2 is a section through a collar of the outer sleeve part showing a portion of the track provided on the inside surface of the outer sleeve part.

As shown in the section of FIG. 2 showing a portion of the inside surface of the collar 6, the track 14A incorporates a slot 15 extending through the wall of the collar 6. When the collar 6 is fitted within the recess 7 in the end of the outer sleeve part 5, the slot 15 forms a channel which communicates with a portion of the track 14A formed by a rectilinear channel 16 in the inside wall of the outer sleeve part 5, as shown diagrammatically in broken lines in FIG. 2. During assembly of the sleeve 1 before the collar 6 is fitted in the end of the outer sleeve part 5, the projection 14 on the inner sleeve part 3 is introduced into a position 20, as shown in broken lines, within the slot 15 in which it is in engagement with a shoulder 22. This requires some deformation of the wall of the collar 6 so that, when the projection 14 is seated within the slot 15 and the collar 6 is subsequently fitted in the recess 7 in the outer sleeve part 5, the projection 14 can no longer be moved out of the track 14A.

When the sleeve 1 is fully assembled, the location of the projection 14 in the position 20 retains the inner sleeve part 3 in a partially contracted position in which the point of the needle 2 projects slightly from the aperture 11. The accessory may be supplied to the user in this state, a removable cap 40 (see FIG. 1) having internal ribs 41 being provided as an interference fit on the end of the sleeve 1 to shield the point of the needle 2. When an injection is to be performed, with the sleeve 1 attached to the outlet of a syringe which is prefilled with injectate, the cap 40 is removed to expose the point of the needle 2, and the point of the needle 2 may then be accurately positioned at the injection site, for example at the site of a vein.

In a modification shown in broken lines in FIG. 2, the projection 14 is initially in a temporary catch position 17 defined by an extension 19 of the slot 15 so that the inner sleeve part 3 is initially in its extended position shielding the point of the needle 2 (in which case a removable cap is not required). In use of this modification the point of the needle 2 is exposed for location at the injection site by manually grasping the inner sleeve part 3 and applying a slight twist to snap the projection 14 out of the temporary catch position 17, and by then applying slight pressure to telescope the inner sleeve part 3 within the outer sleeve part 5 to cause the projection 14 to travel along the slot extension 19 until a click and a slight twist are felt as the projection 14 engages in the position 20.

After the point of the needle 2 has been located at the required injection site, the action of inserting the needle into the patient will cause the inner sleeve part 3 to telescope within the outer sleeve part 5 by the action of the end of the inner sleeve part 3 being pressed against the skin of the patient. This will cause the projection 14 to move beyond a finger portion 21, which is resiliently displaced to allow free passage for the projection 14, and to travel along the channel 16 on the inside wall of the outer sleeve part 5. Since the channel 16 extends in the direction of the length of the needle, there is no relative twisting between the two sleeve parts during such movement.

On withdrawal of the needle from the patient after the injection has been effected, the projection 14 automatically returns along the track 14A under the effect of the spring 8 as the inner sleeve part 3 moves out of the outer sleeve part 5 on release of the contact pressure between the end of the inner sleeve part 3 and the patient's skin. When the projection 14 contacts the finger portion 21, however, it is directed by the finger portion 21 to a final position 23 which is angularly offset from the position 22. In this final position 23 of the projection 14 the sleeve 1 is in its fully extended position in which it is preferably retained in a manner described below so as to shield the point of the needle 2 and prevent the point of the needle 2 from subsequently being exposed with consequent risk of the user being pricked by the contaminated point of the needle.

Figure 3:
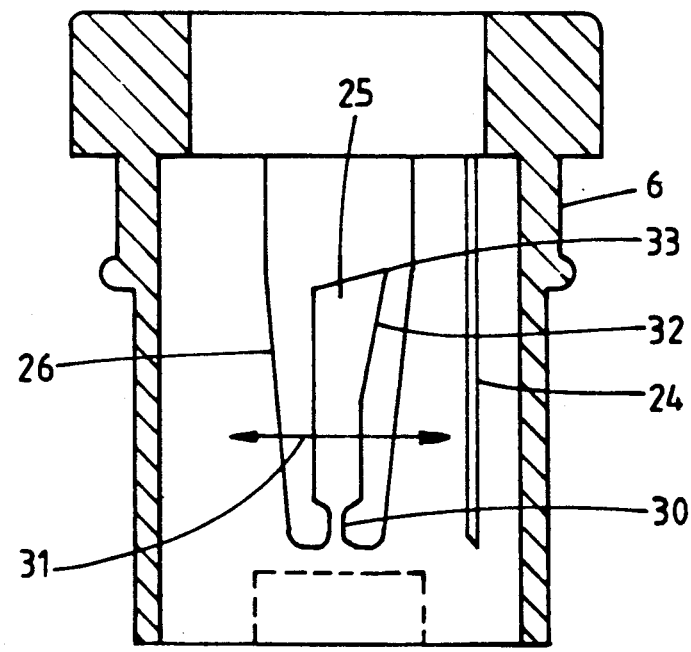
FIG. 3 is a section through the collar showing a locking tongue provided on the inside surface of the outer sleeve part diametrically opposite the track.

The retaining or locking arrangement will now be described with reference to FIGS. 3 to 6. FIG. 3 shows a further portion of the inside surface of the collar 6 having a locking tongue 25 within a cutout 26 in the wall of the collar 6. The locking tongue 25 is joined to the remainder of the collar 6 by a resiliently flexible neck 30 permitting sideways deflection of the locking tongue 25 in the direction of the arrows 31 within the cutout 26. The locking tongue 25 is thicker than the wall of the remainder of the collar 6 so that it projects into a longitudinal recess 27 (see FIGS. 4 and 6) in the outside surface of the inner sleeve part 3 which extends from the level of the shoulder 12 to the inner end of the inner sleeve part 3. The locking tongue 25 has no effect on the movement of the inner sleeve part 3 within the outer sleeve part 5 until the projection 14 moves to the final position 23 in which the point of the needle 2 is shielded by the sleeve 1.

There is also shown in FIG. 3 a rib 24 on the inside surface of the collar 6 which prevents the inner sleeve part 3 from being twisted relative to the outer sleeve part 5 on removal of the cap 40, due to the fact that the rib 24 and the locking tongue 25 engage opposite sidewalls of the recess 27 when the projection 14 is in the position 20.

Figure 5:
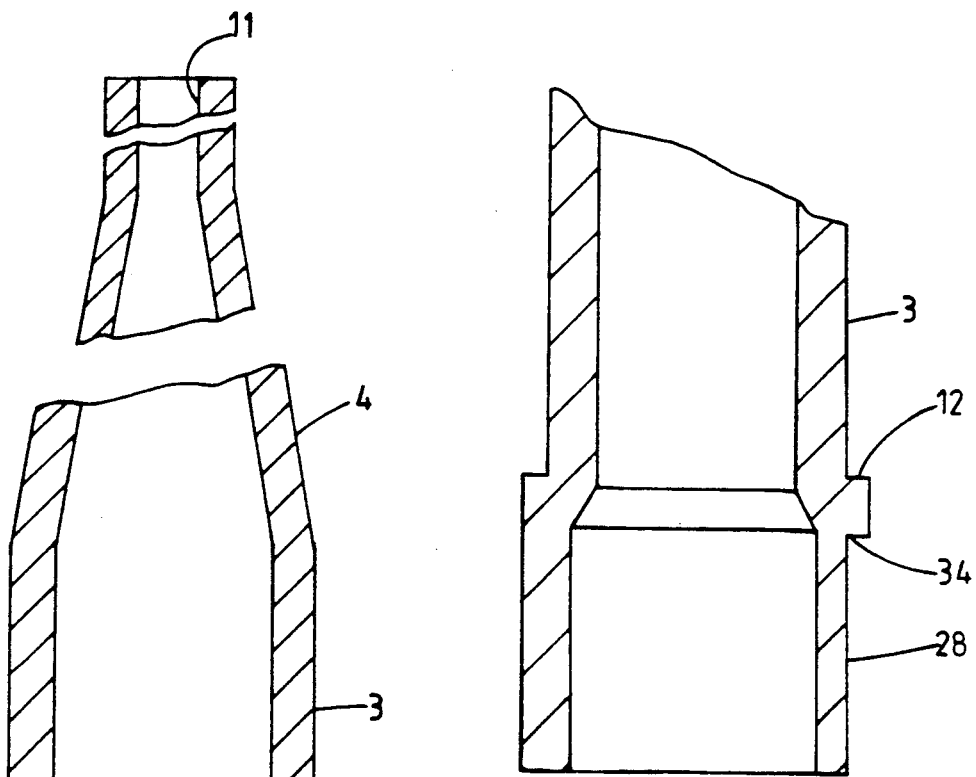
FIG. 5 is a part section through the inner sleeve part taken along the line V—V in FIG. 6.

When the projection 14 contacts the finger portion 21 on the return of the projection 14 along the track 14A after the injection has been effected, the resulting angular displacement of the inner sleeve part 3 relative to the outer sleeve part 5 results in the shoulder 12 on the inner sleeve part 3 contacting the inclined side surface 32 of the locking tongue 25 and displacing the locking tongue 25 sideways in the direction of the arrow 31. At the same time the rib 24 on the inside surface of the collar enters a groove 29 in the outside surface of the inner sleeve part 3. As the projection 14 moves to its final position 23, the shoulder 12 moves beyond the locking nose 33 of the tongue 25, so that the tongue 25 resiliently snaps into a recess 28 which extends from the inner end of the inner sleeve part 3 to a position short of the shoulder 12, as shown in FIG. 5. The locking nose 33 engages beneath a shoulder 34 (see FIG. 5) on the inner sleeve part 3 and prevents the inner sleeve part 3 from being subsequently moved inwardly of the outer sleeve part 5. This locking action will occur even if the neck 30 connecting the locking tongue 25 to the remainder of the collar 6 is fractured since the thickness of the locking tongue 25 will still ensure that the locking tongue 25 serves as a locking wedge.

The above-described locking arrangement has certain advantages in terms of ease of fabrication. However, it should be appreciated that other locking arrangements are possible within the scope of the invention, and in particular alternative locking arrangements can be contemplated in which a locking tongue is provided which is resiliently movable in one or other of the two directions perpendicular to the direction of the arrow 31.

It will be appreciated that this protective sleeve 1 not only guards against needle stick, but also prevents the needle from being used more than once. This is a particularly important feature as it guards against transmission of blood-related diseases by multiple use of needles, and needle stick injuries during use and subsequent disposal. Furthermore, if the sleeve is integrally formed with the syringe or is attached to the syringe in such a manner that it cannot be subsequently removed, this also prevent the syringe from being used more than once.

In a modification the described locking arrangement is dispensed with so that the point of the needle can be re-exposed for re-use by pushing the inner sleeve part 3 within the outer sleeve part 5, preferably after disengagement of a temporary lock preventing the point of the needle from being exposed solely by application of pressure to the end of the sleeve.

Other modifications are possible, for example where the sleeve is to be used for taking a sample of blood from a patient. Where the sleeve is to be used in an evacuated blood collection system, instead of the sleeve being adapted for connection to a syringe it may be formed with an extension to the needle provided with a second point and covered with a rubber sleeve closed at one end which projects beyond the second point of the needle. In this known system for taking blood, the second point of the needle is caused to pierce the closure of an evacuated tube after the first point of the needle has been introduced into the patient so as to cause blood to be drawn along the needle into the tube, the rubber sleeve acting as a valve to prevent blood leaking from the needle when the needle is removed from the tube.

In a further modification the inner sleeve part is adapted to be temporarily retained within the outer sleeve part in a fully contracted position in which the point of the needle is exposed, this being achieved by locking of the projection in a specially adapted portion of the track, for example. This temporary locking can be overcome by twisting of the inner sleeve part to cause the sleeve to adopt its extended position shielding the point of the needle.

Figure 6:
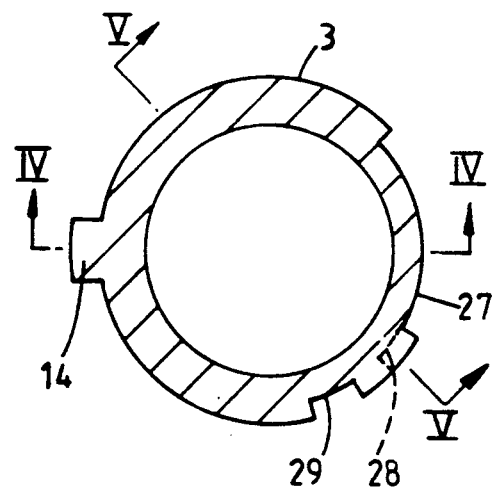
FIG. 6 is a cross-section taken along the line VI—VI in FIG. 4.

The protective sleeve described with reference to the drawings may also be used in a composite sleeve/syringe arrangement of the type described with reference to FIGS. 6 and 7 of European Patent Specification No. 0268445A.

I claim:

1. An accessory for an injection device in which liquid is drawn or expelled along a hollow needle, said accessory comprising: a protective sleeve for surrounding the needle and having two sleeve parts which are movable relative to one another in the direction of the length of the needle from a contracted position, in which the point of the needle projects from the sleeve to an extent to enable an injection to be effected, to an extended position, in which the point of the needle is located within the sleeve to shield the point of the needle, said two sleeve parts constituting an inner sleeve part (3) and an outer sleeve part (5), said two sleeve parts being guided relative to one another by a projection (14) on one sleeve part engaging within a track (14A) in the other sleeve part, at least a portion of the track (14A) being formed by a slot (15) extending through the wall of a collar (6) forming a portion of said other sleeve part, said collar being separately formed from the remainder of said other sleeve part and being fitted to an end portion of the remainder of said other sleeve part when the accessory is assembled.

2. An accessory according to claim 1, wherein the projection (14) is provided on an outer surface of the inner sleeve part (3) and the track (14A) is provided in an inner surface of the outer sleeve part (5), said collar (6) forms a portion of the outer sleeve part (5) and being fitted within an end portion of the remainder of the outer sleeve part (5).

3. An accessory according to claim 1, wherein the slot (15) extending through the wall of the collar (6) defines a shoulder portion (22) with which the projection (14) engages in order to retain the sleeve in a partially contracted position in which the point of the needle (2) projects from the sleeve only to an extent necessary to enable the point of the needle to be located at the intended site of injection.

4. An accessory according to claim 1, wherein the slot (15) extending through the wall of the collar (6) defines a resilient finger portion (21) adapted to be resiliently deflected by the projection (14) to permit passage of the projection along the track (14A) when the sleeve moves into the contracted position, and adapted to subsequently cause the projection to be directed to an angularly offset position (23) when the projection moves back along the track on movement of the sleeve into the extended position.

5. An accessory according to claim 1, wherein a locking tongue (25) is provided within a cutout (26) in the wall of the collar (6) so as to be engageable with a shoulder (34) on said one sleeve part to retain the sleeve in the extended position after the injection has been effected.

6. An accessory according to claim 5, wherein the locking tongue (25) is thicker than the wall of the remainder of the collar (6).

7. An accessory according to claim 5, wherein the locking tongue (25) is connected to the remainder of the collar (6) by a resiliently flexible neck (30) permitting resilient sideways deflection of the locking tongue.

8. An accessory according to claim 3, wherein a detachable cap (40) is provided for attachment to the sleeve to shield the point of the needle (2) when the sleeve is initially retained in the partially contracted position.

9. An accessory for an injection device in which liquid is drawn or expelled along a hollow needle, said accessory comprising: a protective sleeve for surrounding the needle and having two sleeve parts which are movable relative to one another in the direction of the length of the needle from a contracted position, in which the point of the needle projects from the sleeve to an extent to enable an injection to be effected, to an extended position, in which the point of the needle is located within the sleeve to shield the point of the needle, in which retaining means (22) for retaining said sleeve in a partially contracted position in which the point of the needle (2) projects from the sleeve only to an extent necessary to enable the point of the needle to be located at the intended site of injection, said two sleeve parts (3, 5) being guided relative to one another by a projection (14) on one sleeve part engaging within a track (14A) in the other sleeve part, said track including a substantially straight portion (16) along which the projection (14) travels when the sleeve moves from its partially contracted position to its contracted position, said track portion (16) being enclosed by the sleeve so that the projection (14) is not accessible from outside the sleeve, and said track portion (16) extending in the direction of the length of the needle so that there is no relative twisting between the two sleeve parts as the sleeve moves from its partially contracted position to its contracted position.

10. An accessory for an injection device in which liquid is drawn or expelled along a hollow needle, said accessory comprising: a protective sleeve for surrounding the needle and having two sleeve parts which are movable relative to one another in the direction of the length of the needle from a contracted position, in which the point of the needle projects from the sleeve to an extent to enable an injection to be effected, to an extended position, in which the point of the needle is located within the sleeve to shield the point of the needle, retaining means (25, 34) for retaining said sleeve in said extended position after the injection has been effected and for preventing the point of the needle (2) from being exposed solely by application of pressure to the end of the sleeve in the direction of contracting movement, said retaining means including, on one of the sleeve parts (5), a locking tongue (25) within a cutout (26) in the wall of the sleeve part, said locking tongue (25) being pivotal within the cutout (26) between a locking position and a disengaged position and being resiliently biased towards its locking position, and, on the other sleeve part (3), a shoulder (34) positioned such that, during movement of the sleeve from its contracted position to its extended position, said locking tongue (25) overrides the shoulder (34) and, in so doing, is pivoted from its disengaged position into its locking position by resilient action so that it engages behind the shoulder (34) and retains the sleeve in its extended position.

* * * * *